United States Patent [19]

Valentine et al.

[11] Patent Number: 4,906,478

[45] Date of Patent: Mar. 6, 1990

[54] SIMETHICONE/CALCIUM SILICATE COMPOSITION

[75] Inventors: William Valentine; William K. Valentine, both of Lawrenceville, Ga.

[73] Assignee: Valentine Enterprises, Inc., Lawrenceville, Ga.

[21] Appl. No.: 283,310

[22] Filed: Dec. 12, 1988

[51] Int. Cl.[4] .............................................. A61K 33/06
[52] U.S. Cl. .................................................. 424/682
[58] Field of Search ....................................... 424/682

[56] References Cited

U.S. PATENT DOCUMENTS 2,441,098 3/1948 Hyde .
2,774,710 12/1956 Thompson et al. .
3,215,601 11/1965 Stolar .
3,326,754 6/1967 Prussin et al. .
3,401,015 9/1968 Ninger et al. .
3,843,778 10/1974 Diamond et al. .
4,115,553 9/1978 Rubino et al. .
4,127,650 11/1978 Buehler .
4,396,604 8/1983 Mitra .
4,545,989 10/1985 Becker et al. .
4,581,381 4/1986 Morris et al. .
4,605,551 8/1986 Buehler et al. .

Primary Examiner—Shep K. Rose
Attorney, Agent, or Firm—DeLio & Associates

[57] ABSTRACT

An antigas and/or antiflatulent composition comprising an admixture combinate of liquid simethicone and powdered calcium silicate. The simethicone and calcium silicate are blended and sheared to assure a uniform free-flowing powder combined of less than 50 micron particle size. The simethicone and calcium silicate are preferably present in equal amounts by weight. Excipient materials may be blended with the powdered combinate and prepared in a unit dose in the form of a compressed tablet or powder-filled capsule.

6 Claims, No Drawings

SIMETHICONE/CALCIUM SILICATE COMPOSITION

BACKGROUND OF THE INVENTION

This invention relates to a composition and method whereby simethicone is prepared as a dry powder by intermixing it with calcium silicate to form a dry, free-flowing powder of less than 50 micron size suitable for oral administration in tablet, capsule or other form as an antigas ingredient or for use as a defoaming processing aid.

Simethicone is a mixture of polydimethylsiloxane and silica gel suitably purified for pharmaceutical use. The preparation of liquid methylsiloxane polymers are delineated in United States Patent No. 2,441,098, the disclosure of which is hereby incorporated by reference. The normal physical state of simethicone is a water-white to grey, translucent, viscous, oil-like liquid with a density of 0.965–0.970 grams/cubic centimeter having demonstrable immiscibility with water and alcohol.

The medically established therapeutic use for simethicone is as an ointment base ingredient, topical drug vehicle and a skin protectant, but most particularly as an antigas and antiflatulent agent for human application, and an antibloating agent for veterinary application.

Various antacid or antigas formulations, some containing simethicone, are disclosed in the prior art, including U.S. Pat. Nos. 4,605,551 to Buehler et al; U.S. Pat. No. 3,326,754 to Prussin et al; U.S. Pat. No. 2,774,710 to Thompson et al; U.S. Pat. No. 4,115,553 to Rubino et al; U.S. Pat. No. 4,396,604 to Mitra; and U.S. Pat. No. 4,581,381 to Morris et al.

The preferred pharmaceutical solid dose delivery system for an antigas and antiflatulent agent such as simethicone is in the form of a chewable tablet. Such chewable tablets often contain antacid ingredients such as calcium carbonate, aluminum hydroxide, magnesium hydroxide, and magnesium carbonate.

It is extremely troublesome to distribute the oil-like, viscous, water and alcohol immiscible simethicone expeditiously and uniformly throughout a tablet granulation prior to compression. It is equally difficult to be certain that simethicone is in a sufficiently divided and dispersed state so that its action will be quick and effective when administered per os as a chewable or swallowable tablet or powder-filled capsule.

Bearing in mind the problems and deficiencies of the prior art, it is therefore an object of the present invention to provide an effective simethicone-containing powder for use in antacid, antigas and/or antiflatulent formulations.

It is another object of the present invention to provide a facile method of producing an effective simethicone-containing powder utilizing conventional equipment at relatively low cost.

It is a further object of the present invention to provide a simethicone-containing powder for use in formulations which, after processing, retain acceptable defoaming activity.

The present invention achieves these objects and satisfies the long felt need to overcome the difficulties in utilizing simethicone in tablet or capsule preparations. A larger amount of simethicone can be incorporated on calcium silicate by the method of this invention than has previously been disclosed in the prior art. The extremely small particle size of the simethicone-containing powder, established as less than 50 microns, makes it possible to have uniform distribution of the simethicone by simple mixing.

SUMMARY OF THE INVENTION

The present invention relates to simethicone prepared as a dry powder by intermixing it with calcium silicate whereby a dry, free-flowing simethicone-containing powder of less than 50 microns can be readily formed. The simethicone is added in liquid form to powdered calcium silicate whereupon the simethicone is admixed or combined with the calcium silicate. This combinate of liquid simethicone and powdered calcium silicate is blended until uniform, and then sheared to assure complete distribution. The simethicone-containing combinate may be easily added to conventional product bases and then formed into unit dosage tablets or capsules. It is preferred that the simethicone have a 50—50 weight percent mixture with the calcium silicate. This mixture is especially applicable to antacid/anti-gas formulations since the calcium silicate itself has some inherent acid consuming capacity.

DETAILED DESCRIPTION OF THE INVENTION

The preferred simethicone used herein is simethicone U.S.P. as defined in the United States Pharmacopeia, incorporated herein by reference, which has the chemical structure:

$(CH_3)_3Si\ [OSi(CH_3)_2]_nCH_3 + SiO_2$ and the chemical formula: alpha(trimethylsilyl)-omega-methylpoly[oxy(dimethylsilylene)] in mixture with silicon dioxide. Simethicone is a mixture of fully methylated linear siloxane polymers containing repeating units of the formula $[—(CH_3)_2SiO\ —]_n$, stabilized with trimethylsiloxy end-blocking units of the formula $[(CH_3)_3SiO—]$, and silicon dioxide. It is preferred to contain not less than 90.5 percent and not more than 99.0 percent of polydimethylsiloxane $([—(CH_3)_2SiO—]_n)$, and not less than 4.0 percent and not more than 7.0 percent of silicon dioxide.

Calcium silicate occurs as $Ca_2SiO_4$, $Ca_3Si_2O_7$, $Ca_3(Si_3O_9)$ and $Ca_4(H_2Si_4O_{13})$ with various percentages of water of crystallization. Calcium silicate minerals are known by various names including larnite, hillebrandite, foshagite, afwillite, foshallasite, gjellebaekite, grammite, table spate, wollastonite, xonaltite, xonotlite, eaklite and calcium pectolith. Commercial synthetic calcium silicates sold for industrial use include the product family sold by the Manville Corp. under the trademark Micro-Cel. The synthetic calcium silicates useful for this invention are any of a number of commercially available calcium silicates formed as a hydrous calcium silicate produced by the hydrothermal reaction of diatomaceous silica, hydrated lime and water. Such synthetic calcium silicate described herein would have a total surface area of from about 50 to about 190 square meters per gram and a particle size of from about 5 to about 20 microns.

The present invention is specifically directed to a process for the incorporation of simethicone into a fine powder for incorporation into, for example, tablets or capsules. In particular, it is directed to a method for transforming the liquid simethicone to a fine 50% by weight powder by combining it with calcium silicate. The calcium silicate/simethicone combinate powder is readily formulated into tableted antacid or antigas formulations by adding the 50% simethicone active powder mixture to a compressible granule base. The calcium silicate is itself compressible and therefore may be added without sacrificing the compression character of the granule base. It is a further feature of the present invention that the calcium silicate portion of the simethicone active powder mixture is itself an active antacid substance with definable acid consuming capacity.

The method of the present invention may be practiced by obtaining desired quantities of solid calcium silicate, generally found as a powder in its synthetic form, and liquid simethicone U.S.P. These two starting materials are then mixed to produce an essentially uniform, blended combinate. The combinate is sheared or otherwise processed to assure ultimate and uniform distribution of the simethicone.

The preferred relative amounts of the simethicone and calcium silicate are from about 40 to about 60 weight percent simethicone and from about 60 to about 40 weight percent calcium silicate. This range of the ingredients has been found to provide optimum performance of the final powdered product. If more than about 60% by weight calcium silicate is used, the product tends to be too dusty. If more than about 60% by weight simethicone is used, the product tends to be too heavy or moist. Exceeding either extreme will tend to result in poor product performance, most particularly in final tableting. A 1 to 1 equal ratio of simethicone to calcium silicate represents the preferred product performance. While not wishing to be limited to a particular theory, it is believed that sorption, i.e., absorption or adsorption, takes place during blending whereupon simethicone (the sorbate) is taken up by the calcium silicate (the sorbent).

The simethicone-containing powders of the present invention have been found to be equal in foam inhibition and foam breaking to an equivalent amount of simethicone U.S.P. This means that, for example, 40 mg of the 50% simethicone powder is equivalent in performance to 20 mg of simethicone U.S.P. To restate, the 50% simethicone powder has foam suppression action equivalent to the amount of simethicone U.S.P. contained therein, without any degradation of performance due to its combination with the calcium silicate.

Defoaming activity in the mixture, i.e., foam inhibition and foam breaking, may be defined and measured by the procedure given in the United States Pharmacopeia. First, a Foaming Solution and Test Preparation are prepared, as follows:

Foaming Solution - Dissolve 1 g of octoxynol 9 in 100 ml of water.

Test Preparation - Transfer 200 mg of simethicone to a 60 ml bottle, add 50 ml of tertiary butyl alcohol, cap the bottle, and shake vigorously. The preparation may be warmed slightly, if necessary, to effect the solution.

The procedure for determining defoaming activity is as follows: For each test, a clean, unused 250 ml glass jar fitted with a 50-mm cap should be employed. Add, dropwise, 0.5 ml of the Test Preparation to the 250 ml glass jar containing 100 ml of Foaming Solution. Cap the jar and clamp it in an upright position on a wrist-action shaker. Employing a radius of 13.3±0.4 cm (measured from center of shaft to center of bottle), shake for 10 seconds through an arc of 10 at a frequency of 300±30 strokes per minute. Record the time required for the foam to collapse. The time, in seconds, for foam collapse is determined at the instant the first portion of foam-free liquid surface appears, measured from the end of the shaking period. This time is the defoaming activity time and should not exceed 15 seconds for acceptable simethicone activity.

Not only will the calcium silicate/simethicone powder combinate be a fine, grit-free particulate powder that is compressible and that demonstrates antacid properties, but the simethicone therein will also be biologically available in vivo.

The simethicone-containing calcium silicate powder of the present invention can be subsequently combined with any standard unit dose antacid preparation. The simethicone-containing calcium silicate powder may also be used as the sole active ingredient in an anti-gas tablet, granule or capsule preparation.

Other standard excipient, filler or base materials can be added to the simethicone/calcium silicate powder mixture to prepare such preparations in the form of tablets or powder-filled capsules. For preparing tablets, the mixture may be combined and blended with standard compression granules comprising, for example, calcium carbonate, dextrose, aluminum hydroxide dried gel, magnesium hydroxide powder, mannitol/sorbitol, sucrose, any compatible spray dried flavor, and magnesium stearate. The blended preparation may be pressed by standard, well-known techniques to form tablets of desired hardness. A single dosage tablet or capsule may preferably contain from about 25 to 50 mg of the simethicone/calcium silicate mixture, but any desired amount outside of this range may be used for specific applications.

There is no fixed quantity of simethicone which may be used to prepare an antacid/antigas preparation. A typical formulation would contain:

| | |
|---|---|
| Aluminum Hydroxide | 200 mg |
| Magnesium Hydroxide | 200 mg |
| Simethicone/calcium silicate mixture | 25 mg |

Unit dose tablets of antacid/antigas preparations containing the simethicone/calcium silicate combinate of the present invention have been found to have a higher acid-neutralizing capacity than those tablets produced without the combinate. Acid-neutralizing capacity may be measured by the procedure set forth in the United States Pharmacopeia. The procedure, to be conducted at a temperature of 37° C.±3° C., is as follows: First, standardize a pH meter using 0.05m potassium biphthalate and 0.05m potassium tetraoxalate standardizing buffers. Next, transfer 100ml of water to a 250ml ml beaker containing a 40×10 mm magnetic stirring bar that is coated with solid perfluorocarbon and has a spin ring at its center. The power setting of the magnetic stirrer should be adjusted to produce a stirring rate of 300+30 rpm when the stirring bar is centered in the beaker, as determined by a suitable optical tachometer.

The test preparations are prepared as follows:

Powders - Transfer the accurately weighed portion of the substance to be tested to a 250 ml beaker, add 70 ml of water, and mix on the magnetic stirrer for one minute.

Tablets-Weigh not less than 20 tablets and determine the average tablet weight. Grind the tablets to a powder that passes through a No. 20 sieve and is retained on a No. 100 sieve. Mix the material on the No. 100 sieve to obtain a uniform mixture, transfer an accurately weighed quantity of it, equivalent to the minimum dosage, to a 250 ml beaker. If wetting is desired, add not more than 5ml of alcohol (neutralized to an apparent pH of 3.5), and mix to wet the specimen thoroughly. Add 70 ml of water, and mix on the magnetic stirrer for one minute.

The test procedure is as follows:

Pipet 30.0 ml of 1.0N hydrochloric acid VS into the test preparation prepared earlier while continuing to stir with the magnetic stirrer. Magnetic stirring should continue for 15 minutes (accurately timed) after the addition of the acid. Thereafter, begin to titrate immediately, in a period not to exceed 5 minutes, the excess hydrochloric acid with 0.5 N sodium hydroxide VS to attain a stable pH of 3.5 for not less than 15 seconds. Calculate the number of mEq of acid consumed per gram of the substance tested. Each ml of 1.0 N hydrochloric acid is equal to 1 mEq of acid consumed.

EXAMPLES

The following specific examples are given to more precisely and particularly illustrate the specific details of the present invention. Equivalent procedures and quantities will occur to those skilled in the art and therefore, the following examples are not meant to define the limits of the present invention, these being defined only by the scope of the appended claims.

Example 1

| Example 1 | |
|---|---|
| Starting Materials: | |
| Simethicone U.S.P. | 100 g |
| Micro-Cel brand Calcium silicate | 100 g |

The calcium silicate was charged into a 500 cc stainless steel beaker. The simethicone was added slowly with intermittent blending. The blended material was screened through a 30 mesh screen and then run in a reversible high shear mixer for 2 minutes. The resulting powder was smooth, lump free and less than 50 microns in size.

The sample was used to prepare chewable antacid tablets using 40 mg of the simethicone-containing powder per tablet (equivalent to 20 mg of simethicone per tablet.)

Example 2

| Starting Materials: | |
|---|---|
| Simethicone U.S.P. | 100 g |
| Micro-Cel brand Calcium silicate | 100 g |

The calcium silicate was charged into a reversible high shear mixer. The mixer was energized at low speed and the simethicone added over a period of approximately 5 minutes. The resulting powder was smooth, lump free, and less than 50 microns in size.

The sample was used to prepare chewable tablets containing 160 mg of the simethicone-containing powder per tablet (equivalent to 80 mg of simethicone U.S.P. per tablet.)

The simethicone-containing powders from Example 1 and Example 2 were subjected to both standard foam breaking and foam inhibition evaluations using simethicone U.S.P. as the control. The simethicone containing powders were equal in foam inhibition and foam breaking to an equivalent amount of simethicone U.S.P.

Example 3

Micro-Cel brand calcium silicate in the amount of 40 kg was charged into a ribbon mixer. The mixer was energized and 40 kg of simethicone U.S.P. were added on the rising side of the powder flow. The addition of the simethicone took approximately 10 minutes. The mixer was allowed to run an additional 10 minutes and the simethicone-containing powder was discharged into holding drums. The powder from the holding drums was passed through a Fitzpatrick comminuting mill (Model D) set with knives forward at high speed and fitted with a 0.125" holed screen. The sheared material was returned to the ribbon blender and blended for an additional 10 minutes. The resulting simethicone/calcius silicate powder was analyzed as follows:

| Petroleum ether extractables | 49.7% by weight |
|---|---|
| Moisture content (via Computrac) | 2.7% by weight |
| Quantity passing 325 mesh (U.S. sieve) | 100.0% |
| Foam suppression | satisfactory |
| Foam inhibition | satisfactory |

Example 4

Micro-Cel brand calcium silicate in the amount of 10 kg was charged into a 3 cubic foot Lodige mixer equipped with a high speed chopper device (for high shear, high energy blending). With both the main mixing shaft and high speed chopper energized, 10 kg of simethicone U.S.P. were added to the calcium silicate. High shear mixing continued for a period of 5 minutes following the introduction of the simethicone.

The simethicone/calcium silicate powder was analyzed as follows:

| Petroleum ether extractables | 49.3% by weight |
|---|---|
| Moisture content (via Computrac) | 2.9% by weight |
| Quantity passing 325 mesh (U.S. sieve) | 100.0% |
| Foam suppression | Satisfactory |
| Foam inhibition | Satisfactory |

Example 5

Simethicone-containing powders produced according to the procedures in Example 3 and Example 4 were evaluated in the following formulation:

| Compression granules (65% calcium carbonate, 35% sucrose) | 1540 mg |
|---|---|
| Spray dried flavor | 3 mg |
| Magnesium stearate | 7 mg |
| Simethicone/calcium silicate powder | 40 mg |

Tablets were pressed at 1590 mg at a hardness of 6-8 Kp.

As a control, the following formulation, without the simethicone/calcium silicate powder, was prepared:

| | |
|---|---|
| Compression granules (65% calcium carbonate, 35% sucrose) | 1540 mg |
| Spray dried flavor | 3 mg |
| Magnesium stearate | 7 mg |

Tablets were pressed at 1550 mg at a hardness of 6-8 Kp.

The tablets produced from either trial, i.e., with and without the simethicone/calcium silicate powder, satisfied criteria for taste acceptance, mouth feel, hardness, friability, and acid neutralization.

Discernible differences were:

1. The chemical assay establishing mEq of HCl for neutralization was higher for the tablets formulated with the simethicone/calcium silicate powder, and 2. The standard physical evaluation for the suppression of foam demonstrated that the tablets formulated with the simethicone/calcium silicate powder displayed satisfactory foam suppression while the tablets lacking the simethicone/calcium silicate powder did not display satisfactory foam suppression.

Example 6

Simethicone/caccium silicate powders produced according to the procedures in Example 3 and Example 4 were evaluated int he following formulations:

| | |
|---|---|
| Compression dextrose | 748 mg |
| Aluminum hydroxide dried gel | 200 mg |
| Magnesium hydroxide powder | 200 mg |
| Simethicone/calcium silicate powder | 40 mg |
| Spray dried flavor | 5 mg |
| Magnesium stearate | 7 mg |

Tablets were pressed at 1200 mg at a hardness of 6-8 Kp.

As a control, the following formulation, without the simethicone/calcium silicate powder, was prepared:

| | |
|---|---|
| Compression dextrose | 788 mg |
| Aluminum hydroxide dried gel | 200 mg |
| Magnesium hydroxide powder | 200 mg |
| Spray dried flavor | 5 mg |
| Magnesium stearate | 7 mg |

Tablets were pressed at 1200 mg at a hardness of 6-8 Kp.

The tablets produced from either trial, i.e., with and without simethicone/calcium silicate powder satisfied the criteria for taste acceptance, mouth feel, hardness, friability and acid neutralization.

Discernable differences were:

1. The chemical analysis establishing mEq of HCl required for neutralization was higher for the tablets formulated with the simethicone/calcium silicate powder, and 2. The physical evaluation for the suppression of foam demonstrated that the tablets formulated with the simethicone/calcium silicate powder displayed satisfactory foam suppression while the tablets lacking the simethicone/calcium silicate powder did not display satisfactory foam suppression.

Example 7

Simethicone/calcium silicate powders produced according to the procedures in Example 3 and Example 4 were evaluated in the following formulation:

| | |
|---|---|
| Dextrose compression granules | 748 mg |
| Aluminum magnesium hydrate with magnesium sulfate | 400 mg |
| Simethicone/calcium silicate powder | 40 mg |
| Spray dried flavor | 5 mg |
| Magnesium stearate | 7 mg |

Tablets were pressed at 1200 mg at a hardness of 6-8 Kp.

The tablets produced satisfied the criteria for taste acceptance, mouth feel, hardness, friability, acid neutralization and foam suppression Example 8

Simethicone/calcium silicate powders produced according to the procedures in Example 3 and Example 4 were evaluated in the following formulations:

| | |
|---|---|
| Mannitol/sorbitol compression granules | 1028 mg |
| Simethicone/calcium silicate powders | 160 mg |
| Spray dried flavor | 5 mg |
| Magnesium stearate | 7 mg |

Tablets were pressed at 1200 mg at a hardness of 6-8 Kp.

The tablets produced satisfied the criteria for taste acceptance, mouth feel, hardness, friability and foam suppression.

While this invention has been described with reference to specific embodiments, it will be recognized by those skilled in the art that variations are possible without departing from the spirit and scope of the invention, and that it is intended to cover all changes and modifications of the invention disclosed herein for the purposes of illustration which do not constitute departure from the spirit and scope of the invention.

Having thus described the invention, what is claimed is:

What is claimed:

1. A consumable antigas and/or antiflatulent composition comprising a powdered combinate of particulate calcium silicate and simethicone, wherein said simethicone is taken up by the calcium silicate particles by sorption, wherein said calcium silicate comprises about 40 to 60 percent, and said simethicone comprises about 60 to 40 percent, by weight, of said powdered mixture, and wherein said powdered combinate has a particle size of less than 50 microns.

2. The composition of claim 1 further including one or more excipients blended with said powdered combinate.

3. The composition of claim 2 wherein said powdered mixture is prepared in a unit dosage of the form of a compressed tablet or powder-filled capsule.

4. A consumable antigas, and/or antiflatulent composition comprising a free-flowing powdered combinate prepared in a unit dosage in the form of a compressed tablet or powder-filled capsule of equal amounts of synthetic calcium silicate particles and simethicone U.S.P., said powdered combinate having a particle size of less than 50 microns.

5. The composition of claim 4 further including one or more suitable excipients.

6. The composition of claim 5 wherein said excipient is chosen from the group consisting of calcium carbonate, dextrose, sucrose, aluminum hydroxide, magnesium hydroxide, magnesium stearate, mannitol, sorbitol, and combinations thereof.

* * * * *

UNITED STATES PATENT AND TRADEMARK OFFICE
CERTIFICATE OF CORRECTION

PATENT NO. : 4,906,478

DATED : March 6, 1990

INVENTOR(S) : William K. Valentine and William Valentine

It is certified that error appears in the above-identified patent and that said Letters Patent is hereby corrected as shown below:

Title page:

In the Abstract line 5, delete "combined" and substitute therefore --combinate--.

In the Specification

Column 4, line 57, delete "+" and substitute therefor --±--
Column 7, line 29, delete "int he" and substitute therefor --in the--

Signed and Sealed this

Eighth Day of January, 1991

Attest:

HARRY F. MANBECK, JR.

*Attesting Officer*      *Commissioner of Patents and Trademarks*